(12) United States Patent
Aantaa et al.

(10) Patent No.: US 6,716,867 B1
(45) Date of Patent: Apr. 6, 2004

(54) USE OF DEXMEDETOMIDINE FOR ICU SEDATION

(75) Inventors: Riku Aantaa, Turku (FI); Romeo Bachand, Mundelain, IL (US); Esa Heinonen, Turku (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/647,364

(22) PCT Filed: Mar. 31, 1999

(86) PCT No.: PCT/FI99/00266
§ 371 (c)(1),
(2), (4) Date: Dec. 6, 2000

(87) PCT Pub. No.: WO99/49854
PCT Pub. Date: Oct. 7, 1999

Related U.S. Application Data
(60) Provisional application No. 60/080,287, filed on Apr. 1, 1998, and provisional application No. 60/110,944, filed on Dec. 4, 1998.

(51) Int. Cl.$^7$ .............................................. A61K 31/415
(52) U.S. Cl. ........................................................ 514/396
(58) Field of Search ......................................... 514/396

(56) References Cited

U.S. PATENT DOCUMENTS 4,910,214 A 3/1990 Karjalainen et al.

FOREIGN PATENT DOCUMENTS

EP  0 413 487 A1  2/1991
EP  0 424 059 A1  4/1991

OTHER PUBLICATIONS

CA 130:231765, Caudwell et al, Int. Congr. Symp. Ser.—R. Soc. Med. 1998, 221, 73–81, abstract.*
CACA130:246080, Mantz et al, Int. Congr. Symp. Ser.—R. Soc. Med. 1009, 221, 23–29, abstract.*
EMBASE AN 1997328166, Celorrio et al, Actualizaciones en Anestesiologia y Reanimacion, 1997, 7/3, 105–125, abstract.*
Bischoff P. et al. : "[Alpha2–Agonists in Anaesthesia and Intensive–Care Medicine]. Alpha2–Agonisten in Anasthesie und Intensivmedizin." Anasthesiologie Intensivmedizin Notfallmedizin Schmerztherapie, (1993) 28/1 (2–12).
Crippen D. et al.: "Stress, Agitation, and Brain Failure in Critical Care Medicine. " Critical Care Nursing Quaterly, (1992) 15/2 (52–74).
V. Hooper et al., "Sedation in the Critically ill Patient," Critical Care Nursing Clinics of North America, vol. 9, pp. 395–410 (1997).
M. Pepperman, "Benzodiazepine sedation and the use of benzodiazepine antagonists in intensive care," Intensive Therapy and Clinical Monitoring, pp. 58–62 (Feb. 1989).
Abstract of Belleville JP et al., "Effects of intravenous dexmedetomidine in humans. I. Sedation, ventilation, and metabolic rate", Anesthesiology 1992 Dec., 77(6):1125–1133.
Abstract of Jaakola ML, "Dexmedetomidine premedication before intravenous regional anesthesia in minor outpatient hand surgery", J Clin Anesth 1994 May–Jun., 6(3):204–211.
Abstract of Werner C., "Effects of analgesia and sedation on cerebrovascular circulation, cerebral blood volume, cerebral metabolism and intracranial pressure", Anaesthesist 1995 Dec., 44 Suppl 3:S566–572.
Abstract of Vulliemoz Y., Shen H., Virag L., "Alpha–2 adrenoceptor agonists decrease cyclic guanosine 3',5'-monophosphate in the mouse brain", Anesthesiology 1996 Sep., 85(3):544–550.
Abstract of Ip Yam PC, Forbes A., Kox WJ., "Clonidine in the treatment of alcohol withdrawal in the intensive care unit", Br J Anaesth 1992 Jan., 68(1):106–108.
Jean Mantz and the French Dexmedetomidine Phase III Study Group, "Phase III Study On Dexmedetomidine Used For Postoperative Sedation Of Patients Requiring Mechanical Ventilation For Less Than 24 Hours: The French Experience", M.E.J. Anesth 16 (6):597–606, 2002.
Mohamad Said Takrouri et al., "Dexmedetomidine In Intensive Care Unit: A Study Of Hemodynamic Changes", M.E.J. Anesth 16 (6): 587–595, 2002.
R. M. Venn et al., "Pharmacokinetics of dexmedetomidine infusions for sedation of postoperative patients requiring intensive care", British Journal of Anaesthesia 88(5):669–75, 2002.
Mervyn Maze, "Sedation in the intensive care unit", International Congress and Symposium Series No. 221, pp. 3–10, 1998.
Elizabeth Caudwell et al., "Nursing considerations in intensive care unit sedation and experience with dexmedetomidine," International Congress and Symposium Series No. 221, pp. 73–81, 1998.
Celorrio et al Sedacion y relajacion neuromuscular en las unidades de cuidados intensivos, Act. Anest. Reanim, vol. 7, pp. 105–126 (1997) (with accompanying translation of certain sections).
Bohrer, "Clonidine as a sedative adjunct in intensive care," Intensive Care Med, vol. 16, pp. 265–266 (1990).
Doze et al., "Pertussis Toxin and 4–Aminopyridine Differentially Affect the Hypnotic–Anesthetic Action of Dexmedetomidine and Pentobarbital," Anesthesiology, vol. 73, pp. 304–307 (1990).
C.J. Peden et al., "Editorial II: Dexmedetomidine–A powerful New Adjunct to Anaesthesia?," Br. J. Anaesth., vol. 68, pp. 123–125 (1992).
M. Tryba et al., "Critical Care Pharmacotherapy," Drugs, vol. 45, pp. 338–352 (1993).

* cited by examiner

Primary Examiner—Rebecca Cook
(74) Attorney, Agent, or Firm—Finnegan, Henderson, Farabow, Garrett & Dunner, LLP

(57) ABSTRACT

The present invention relates to a method of sedating a patient while in the intensive care unit comprising administering dexmedetomidine of a pharmaceutically acceptable salt thereof to the patient, wherein the patient remains arousable and orientated.

12 Claims, 2 Drawing Sheets

| CLINICAL SCORE | LEVEL OF SEDATION ACHIEVED |
|---|---|
| 1 | PATIENT ANXIOUS, AGITATED OR RESTLESS |
| 2 | PATIENT CO-OPERATIVE, ORIENTED AND TRANQUIL |
| 3 | PATIENT RESPONDS TO COMMANDS |
| 4 | ASLEEP BUT WITH BRISK RESPONSE TO LIGHT GLABELLAR TAP OR LOUD AUDITORY STIMULUS |
| 5 | ASLEEP, SLUGGISH RESPONSE TO LIGHT GLABELLAR TAP OR LOUD AUDITORY STIMULUS |
| 6 | ASLEEP, NO RESPONSE |

*FIG. 1*

USE OF DEXMEDETOMIDINE FOR ICU SEDATION

This application is a national stage filing of PCT International Application No. PCT/FI99/00266, filed on Mar. 31, 1999, which claims priority to U.S. Provisional Application Ser. No. 60/080,287, filed on Apr. 1, 1998, and which also claims priority to U.S. Provisional Application Ser. No. 60/110,944, filed on Dec. 4, 1998.

BACKGROUND OF THE INVENTION

The present invention relates to the use of dexmedetomidine or a pharmaceutically acceptable salt thereof in intensive care unit (ICU) sedation. In addition to the actual sedation of a patient in the ICU, the word sedation in the ICU context also includes the treatment of conditions that affect patient comfort, such as pain and anxiety. Also, the word intensive care unit includes any setting that provides intensive care. Accordingly, the present invention relates to a method of sedating a patient while in the ICU by administering dexmedetomidine or a pharmaceutically acceptable salt thereof. Particularly, the present invention relates to a method of sedating a patient while in the ICU by administering dexmedetomidine or a pharmaceutically acceptable salt thereof, wherein dexmedetomidine is essentially the sole active agent or the sole active agent administered for this purpose. The present invention also relates to the use of dexmedetomidine or a pharmaceutically acceptable salt thereof in the manufacture of a medicament for intensive care unit sedation.

Patients recovering from an episode of critical illness have reported factors they found most distressing during their ICU stay (Gibbons, C. R., et al., Clin. Intensive Care 4 (1993) 222–225). The most consistently unpleasant memories are anxiety, pain, fatigue, weakness, thirst, the presence of various catheters, and minor procedures such as physiotherapy. The aim of ICU sedation is to ensure that the patient is comfortable, relaxed, and tolerates uncomfortable procedures such as placement of iv-lines or other catheters, but is still arousable.

At the moment, there is no universally accepted sedative regimen for critically ill patients. Thus, these patients receive a variety of drugs during their stay in an ICU, often receiving the variety of drugs concurrently The agents used most commonly are given to achieve patient comfort. Various drugs are administered to produce anxiolysis (benzodiazepines), amnesia (benzodiazepines), analgesia (opioids), antidepression (antidepressants/benzodiazepines), muscle relaxation, sleep (barbiturates, benzodiazepines, propofol) and anaesthesia (propofol, barbiturates, volatile anesthetics) for unpleasant procedures. These agents are cumulatively called sedatives in the context of ICU sedation, though sedation also includes the treatment of conditions that affect patient comfort, such as pain and anxiety, and many of the drugs mentioned above are not considered sedatives outside the context of ICU sedation.

The presently available sedative agents are associated with such adverse effects as prolonged sedation or oversedation (propofol and especially poor metabolizers of midazolam), prolonged weaning (midazolam), respiratory depression (benzodiazepines, propofol, and opioids), hypotension (propofol bolus dosing), bradycardia, ileus or decreased gastrointestinal motility (opioids), immunosuppression (volatile anaesthetics and nitrous oxide), renal function impairment, hepatotoxicity (barbiturates), tolerance (midazolam, propofol), hyperlipidemia (propofol), increased infections (propofol), lack of orientation and cooperation (midazolam, opioids, and propofol), and potential abuse (midazolam, opioids, and propofol).

In addition to the adverse effects of every individual sedative agent, the combination of these agents (polypharmacy) may cause adverse effects. For example, the agents may act synergistically, which is not predictable; the toxicity of the agents may be additive; and the pharmacokinetics of each agent may be altered in an unpredictable fashion. In addition, the possibility of allergic reactions increases with the use of more than one agent. Furthermore, these adverse effects might necessitate the use of additional agents to treat the adverse effects, and the additional agents themselves may have adverse effects.

The preferred level of sedation for critically ill patients has changed considerably in recent years. Today, most intensive care doctors in the ICU prefer their patients to be asleep but easily arousable, and the level of sedation is now tailored towards the patient's individual requirements. Muscle relaxants are seldom used during intensive care. As cardiovascular stability is also desired in this often high-risk patient population, hemodynamically active agents are often needed for adequate hemodynamic control despite sufficient sedation.

$\alpha_2$-adrenoceptor agonists are being evaluated in general anaesthetic practice because of their sympatholytic, sedative, anaesthetic, and hemodynamic stabilizing effects. Tryba et al. discussed the usefulness of $\alpha_2$-agonists in situations where patients with withdrawal symptoms are treated in the ICU (Tryba et al., Drugs 45 (3) (1993), 338–352). The only $\alpha_2$-agonist mentioned was clonidine, which was used in conjunction with opioids, benzodiazepines, ketamine, and neuroleptics. Tryba et al. suggest that clonidine may be useful in ICU patients with withdrawal symptoms, but Tryba et al. only briefly mention the use of clonidine for ICU sedation. Furthermore, Tryba et al. only mention clonidine as a supplement to other sedatives for ICU sedation.

According to Tryba et al., clonidine has its limitations in sedating critically ill patients mainly because of its unpredictable hemodynamic effects, i.e., bradycardia and hypotension, so that it must be titrated for each individual patient. Long term treatment of critically ill patients with clonidine has been reported to be associated with such rebound effects as tachycardia and hypertension.

$\alpha_2$-agonists are not presently used by themselves in ICU sedation. Further, $\alpha_2$-agonists are not generally used in ICU sedation even in conjunction with other sedative agents. Only clonidine has been evaluated for use in ICU sedation, and then only in conjunction with opioids, benzodiazepines, ketamine, and neuroleptics. Further, administration of clonidine as essentially the sole active agent or the sole active agent to a patient in the ICU to achieve sedation has not been disclosed to the best of applicants' knowledge.

An ideal sedative agent for a critically ill patient should provide sedation at easily determined doses with ready arousability together with hemodynamic stabilizing effects. Further, it should be an anxiolytic and an analgesic, and should prevent nausea, vomiting, and shivering. It should not cause respiratory depression. Preferably, an ideal sedative agent should be used by itself in ICU sedation to avoid the dangers of polypharmacy.

Dexmedetomidine, or (+)-(S)-4-[1-(2,3-dimethylphenyl)ethyl]-1H-imidazole, has the following formula:

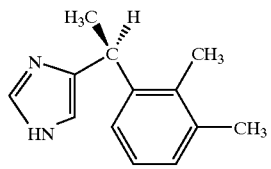

Dexmedetomidine is described in U.S. Pat. No. 4,910,214 as an $\alpha_2$-receptor agonist for general sedation/analgesia and the treatment of hypertension or anxiety. U.S. Pat. Nos. 5,344,840 and 5,091,402 discuss dexmedetomidine in perioperative and epidural use, respectively. U.S. Pat. No. 5,304,569 discusses the use of dexmedetomidine in glaucoma. U.S. Pat. No. 5,712,301 discusses the use of dexmedetomidine for preventing neurodegeneration caused by ethanol consumption.

Medetomidine, which is the racemic mixture of dexmedetomidine and levomedetomidine, is known as a selective and potent $\alpha_2$-agonist and has been described in U.S. Pat. No. 4,544,664 as an antihypertensive agent and in U.S. Pat. No. 4,670,455 as a veterinary sedative-analgesic agent.

In U.S. Pat. Nos. 4,544,664 and 4,910,214, parenteral, intravenous, and oral ways of administration are discussed. U.S. Pat. No. 4,670,455 describes intramuscular and intravenous administration. U.S. Pat. Nos. 5,124,157 and 5,217,718 describe a method and device for administering dexmedetomidine through the skin. U.S. Pat. No. 5,712,301 states that dexmedetomidine can be administered transmucosally.

The U.S. Patents discussed herein are specifically incorporated by reference in their entirety.

SUMMARY OF THE INVENTION

It has been unexpectedly found that dexmedetomidine or a pharmaceutically acceptable salt thereof is an ideal sedative agent to be administered to a patient in the ICU to achieve patient comfort. Accordingly, an object of the invention is to provide a method of sedating a patient while in the ICU that comprises administering dexmedetomidine or a pharmaceutically acceptable salt thereof for a time sufficient to give the desired therapeutic effect.

It should be noted that the method for sedating a patient in the ICU encompasses all of the potential ICU uses of dexmedetomidine and a pharmaceutically acceptable salt thereof, including all potential uses that derive from their activity as $\alpha_2$-agonists, e.g., their use as hypotensive agents, anxiolytics, analgesics, sedatives, and the like. It should also be noted that the word intensive care unit encompasses any setting that provides intensive care.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

In one aspect, the invention relates to a method of sedating a patient while in the ICU by administering dexmedetomidine or a pharmaceutically acceptable salt thereof, wherein dexmedetomidine is essentially the sole active agent or the sole active agent. The method is premised on the discovery that essentially only dexinedetomidine or a pharmaceutically acceptable salt thereof need to be administered to a patient in the ICU to achieve sedation and patient comfort. No additional sedative agents are required.

In a further aspect, the invention relates to a use of dexmedetomidine or a pharmaceutically acceptable salt thereof in ICU sedation.

A further aspect of the invention relates to a use of dexmedetomidine or a pharmaceutically acceptable salt thereof in the manufacture of a medicament for ICU sedation.

It is to be understood that both the foregoing general description and the following detailed description are exemplary and explanatory only and are not restrictive of the invention, as claimed.

BRIEF DESCRIPTION OF THE DRAWINGS

FIG. 1 shows the Ramsay Scale that was developed for the assessment of sedation in experimental subjects. In this system, the level of wakefulness is scored on a scale of 1–6 (Ramsey Sedation Score) based on progressive loss of responsiveness to stimuli ranging from auditory to deep painful stimuli.

DETAILED DESCRIPTION OF THE INVENTION

Figure 2:
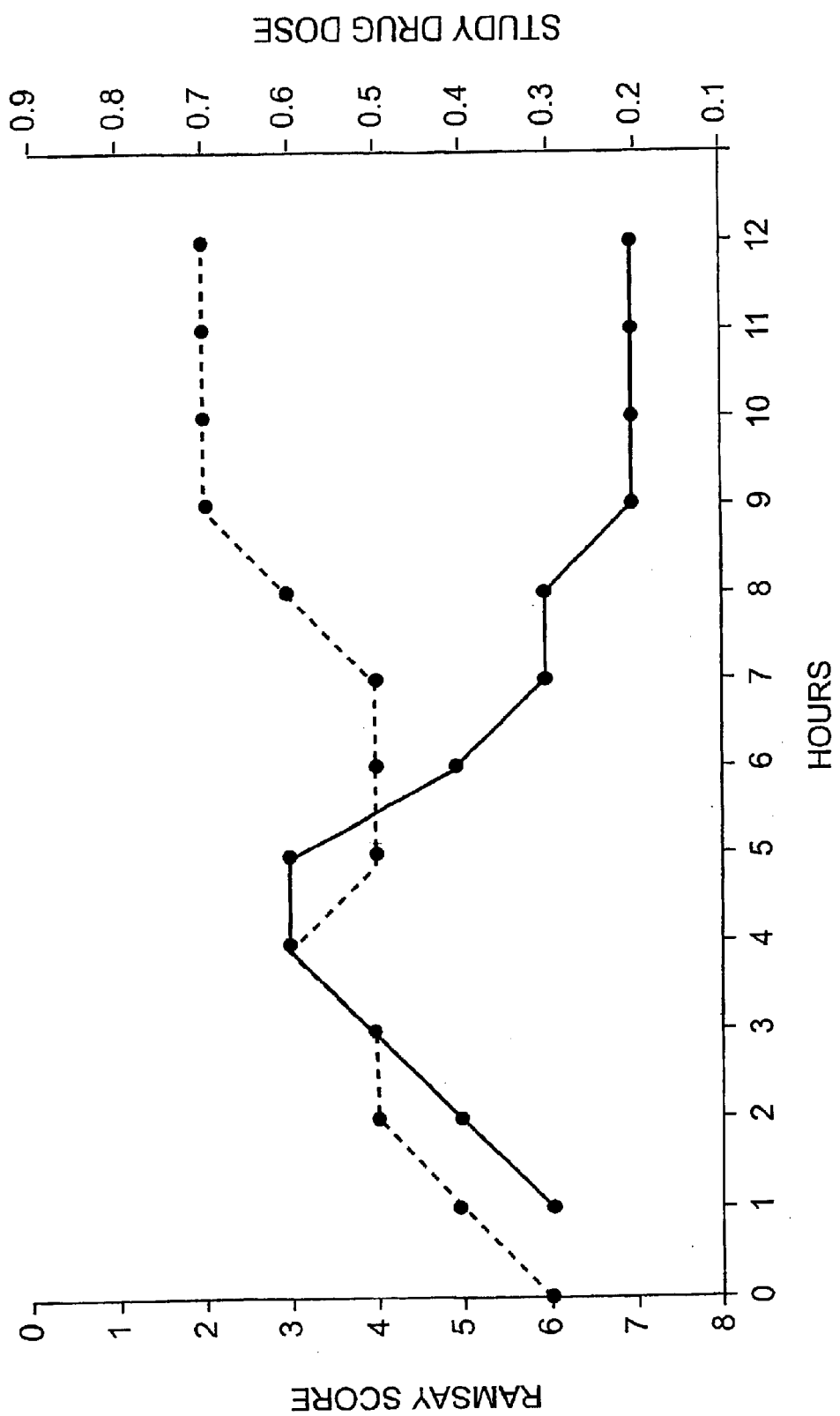
FIG. 2 shows the dosing period from the Phase III dexmedetomidine study described in Example 3, case No. 13. The dotted line signifies Ramsay Sedation Score fluctuations and the solid line signifies dexmedetomidine dose adjustments.

Applicants have surprisingly discovered that dexmedetomidine or a pharmaceutically acceptable salt thereof is an ideal agent to be administered to a patient in the ICU for achieving sedation and patient comfort. Particularly, it has been found that dexmedetomidine or a pharmaceutically acceptable salt thereof can be essentially the sole active agent or the sole active agent administered to a patient in the ICU in order to sedate the patient.

The method for sedating a patient in the ICU encompasses all of the potential ICU uses of dexmedetomidine and a pharmaceutically acceptable salt thereof, including all potential uses that derive from their activity as $\alpha_2$-agonists, e.g., their use as hypotensive agents, anxiolytics, analgesics, sedatives, and the like.

The word intensive care unit encompasses any setting that provides intensive care. The word patient is intended to include both human and animal patients. Preferably, the animal patient is a mammal, especially a dog, a cat, a horse, or a cow.

The quality of the sedation in the ICU achieved by administering dexmedetomidine is unique. Patients sedated by dexmedetomidine or a pharmaceutically acceptable salt thereof are arousable and oriented, which makes the treatment of the patient easier. The patients can be awakened and they are able to respond to questions. They are aware, but not anxious, and tolerate an endotracheal tube well. Should a deeper level of sedation or more sedation be required or desired, an increase in dexmedetomidine dose smoothly transits the patient into a deeper level of sedation. Dexmedetomidine does not have adverse effects associated with other sedative agents, such as, respiratory depression, nausea, prolonged sedation, ileus or decreased gastrointestinal motility, or imnmunosuppression. Lack of respiratory depression should allow dexmedetomidine to be used also for non-ventilated, critically ill patients who require sedation, anxiolysis, analgesia, and hemodynamic stability yet must remain oriented and easily aroused. In addition, it is water soluble and, thus, does not increase the lipid load in patients sedated for long periods of time. A predictable pharmacological response can be achieved by administering dexmedetomidine or a pharmaceutically acceptable salt thereof to a patient in the ICU.

Dexmedetomidine or a pharmaceutically acceptable salt thereof can be administered perorally, transmucosally, transdermally, intravenously or intramuscularly. One skilled in the art would recognize the doses and dosage forms suitable in the method of the present invention. The precise amount of the drug administered according to the invention is dependent on numerous factors, such as the general condition of the patient, the condition to be treated, the desired duration of use, the route of administration, the type of mammal, etc. The dose range of dexmedetomidine can be described as target plasma concentrations. The plasma concentration range anticipated to provide sedation in the patient population in the ICU varies between 0.1–2 ng/ml depending on the desired level of sedation and the general condition of the patient. These plasma concentrations can be achieved by intravenous administration by using a bolus dose and continuing it by a steady maintenance infusion. For example, the dose range for the bolus to achieve the forementioned plasma concentration range in a human is about 0.2–2 $\mu$g/kg, preferably about 0.5–2 $\mu$g/kg, more preferably 1.0 $\mu$g/kg, to be administered in about 10 minutes or slower, followed by a maintenance dose of about 0.1–2.0 $\mu$g/kg/h, preferably about 0.2–0.7 $\mu$g/kg/h, more preferably about 0.4–0.7 $\mu$g/kg/h. The time period for administering dexmedetomidine or a pharmaceutically acceptable salt thereof depends on the the desired duration of use.

The chemical form for dexynedetomidine can be the free base or an acid addition salt. Such acid addition salts may be formed, for example, with inorganic acids, such as, hydrochloric acid, hydrobromic acid, sulfiric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

The invention will be further clarified by the following example, which is intended to be purely exemplary of the invention.

EXAMPLE 1

The efficacy, safety and titratability of dexmedetomidine in postoperative coronary artery bypass graft(s) patients (CABG), requiring sedation in the ICU was studied. The patients were intubated for 8–24 hours. All patients were administered dexmedetomidine within 1 hour of admission to the ICU, and dexmedetomidine infusion was continued until 6 hours after extubation. Dexmedetomidine was used in the form of an HCl salt (100 $\mu$g/ml, base) in 0.9% sodium chloride solution, and it was administered as a two-stage infusion (a loading dose followed by a maintenance infusion) utilizing standard syringe pump and iv administration sets.

12 patients were selected and divided into two groups. The first 6 patients were administered a loading dose of 6 $\mu$g/kg/h of dexmedetomidine over a 10-minute period, followed by a maintenance infusion of 0.2 $\mu$g/kg/h. The second group of 6 patients were initially administered a loading dose of 6.0 $\mu$g/kg/h of dexmedetomidine over a 10 minute period, followed by a maintenance infusion of 0.4 $\mu$g/kg/h. The infusion rate in both groups was maintained between a range of 0.2 to 0.7 $\mu$g/kg/h. After the clinical effects of sedation became evident (approximately within 15 to 30 minutes) the maintenance rate of infusion could be adjusted in increments of 0.1 $\mu$g/kg/h or higher to achieve and maintain a Ramsey Sedation Score level of 3 or higher (see FIG. 1).

Vital signs, adverse events, and sedation scores were recorded during the study. The patients did not receive any of the following medications during the administration of dexmedetomidine: sedating agents, neuromuscular blocking agents except for insertion of the endotracheal tube, and epidural or spinal analgesic/anaesthetic agents. Two patients required morphine for pain. One patient had two serious adverse events: circulatory failure and myocardial infarction. The myocardial infarction, due to incomplete revascularization, led to death 13 days after the study drug infusion had been discontinued. The myocardial infarction had little or no temporal relationship to dexmedetomidine. In fact, incomplete revascularization is one of the most common adverse events after a CABG operation, and it sometimes leads to death.

During the administration of dexmedetomidine, the blood pressure and heart rate variability were decreased, meaning more stable and predictable hemodynamics without the need for pharmacological interventions to either treat high blood pressure or heart rate, e.g., with beta-blockers, or to increase sedation/anxiolysis with benzodiazepins or propofol. In conclusion, the patients were conveniently sedated, hemodynamically stable, and remained easily arousable for control of subjective well being with only one pharmaceutical, dexmedetomidine.

The example shows that dexmedetomidine is an ideal agent for sedating a patient in the ICU, providing a unique quality of sedation and patient comfort.

EXAMPLE 2

A double-blind, randomized, placebo-controlled study was conducted to evaluate the efficacy, safety, and titratability of dexmedetomidine in mechanically ventilated patients requiring sedation in the ICU. The study was conducted in postoperative CABG patients requiring sedation in the ICU. Twelve adult postoperative CABG patients requiring mechanical ventilation in the ICU who met the study selection criteria were eligible for participation.

The selection criteria were as follows. The patients required sedation for mechanical ventilation for a minimum of 8 hours following surgery, followed by continued sedation for 6 hours after extubation. The patients were not to have been intubated longer than 24 hours to be evaluable for the test. The patients received only morphine for management for pain and received none of the following medications during study drug administration: sedating agents other than midazolam, neuromuscular blocking agents except for insertion of the endotracheal tube, epidural or spinal analgesic/anesthetic agents.

Safety was evaluated through the monitoring of adverse events, cardiac monitoring, laboratory tests, vital signs, oxygen saturation, and concomitant medications.

Twelve patients were randomly assigned to receive either dexmedetomidine or placebo with rescue treatment for sedation with midazolam, as clinically indicated. Patients randomized to dexmedetomidine were to receive a 10-minute loading dose of 6.0 $\mu$g/kg/h, followed by an initial maintenance infusion. The rate of maintenance infusion was 0.4 $\mu$g/kg/h. The maintenance rate of infusion could be titrated in increments of 0.1 $\mu$g/kg/h to achieve and maintain a Ramsey Sedation Score of 3 or higher. The range for the maintenance infusion was to be kept between 0.2 and 0.7 μg/kg/h. Dexmedetomidine administration was to begin within one hour after admission to the ICU and continued until 6 hours after extubation. Dexmedetomidine was used in the form of an HCl salt (100 μg/ml, base) in 0.9% sodium chloride solution, and it was administered utilizing standard syringe pump and iv administration sets. The placebo was 0.9% sodium chloride solution administered the same way dexmedetomidine was administered.

The six dexmedetomidine-sedated patients remained adequately sedated and did not require any midazolam. Conversely, five of the six placebo-treated patients required the administration of midazolam to achieve sufficient (Ramsay Sedation Score$\geq$3) levels of sedation (total mean midazolam mg/kg/h$\pm$SEM=0.018$\pm$0.005). The difference between the two treatment groups in mean total dose of midazolam received during the study was statistically significant (p=0.010). The overall level of sedation was comparable between the two groups, but the administration of dexmedetomidine resulted in stable Ramsay Sedation Scores, characterized by minimal variability over time, compared with intermittent sedation (Ramsay Sedation Score$\geq$3) and agitation (Ramsay Sedation Score of 1) among placebo-treated patients.

Dexmedetomidine also demonstrated analgesic properties in this patient population, as measured by the total dose of morphine administered throughout the duration of the study. One of six dexmedetomidine-treated patients required morphine administration for management of pain compared to five of the six placebo-treated patients. The difference between the treatment groups in mean total dose of morphine was statistically significant (p=0.040).

In conclusion, patients treated with dexmedetomidine required significantly less midazolam for sedation or morphine for pain than did patients who received placebo. Sedation levels for dexmedetomidine-treated patients were more stable than those for placebo-treated patients who received midazolam. Dexmedetomidine was safe and well tolerated, and it produced no clinically apparent respiratory depression after cessation of assisted ventilation.

EXAMPLE 3

Two Phase III dexmedetomidine multicenter clinical trials (Trial 1 and Trial 2) have been conducted in ICU sedation in Europe and Canada. Each trial had two parts, i.e., an open-label part (Part I) and double-blind, randomized, placebo-controlled part (Part II). The trials were designed to evaluate the reduction in requirements for ICU sedation (as measured by administration of other sedative/analgesic agents) in patients receiving dexmedetomidine. The use of propofol and morphine for sedation and analgesia, respectively, was evaluated in one trial (Trial 1), and midazolam and morphine in the other trial (Trial 2). A total of 493 patients were enrolled and treated in Trial 1 and 438 patients were enrolled and treated in Trial 2.

In Part I of the trials patients were to be administered a 6.0 μg/kg/h loading dose of dexmedetomidine over a 10-minute period, followed by an initial maintenance infusion of 0.4 μg/kg/h. During Part II of the study, patients were randomly assigned to receive either placebo (0.9% sodium chloride solution) or dexmedetomidine. Dexmedetomidine was used as an HCl salt (100 mg/ml, base) in 0.9% sodium chloride solution, and it was administered utilizing standard syringe pump and iv administration sets. The dexmedetomidine dosing protocol was the same as in the Part I of the study. For both parts of the study, following the initial maintenance infusion, the rate of infusion could have been adjusted in increments of 0.1 μg/kg/h or higher. The infusion rate during intubation was to have been maintained in the range of 0.2 to 0.7 μg/kg/h in order to achieve and maintain a Ramsey Sedation Score of 3 or higher. Following extubation, the infusion rate was to be adjusted to achieve a Ramsay Sedation Score of 2 or higher.

During the 10-minute loading dose, additional medication was to be avoided, but propofol (0.2-mg/kg bolus) in Trial 1 and midazolam (1-mg bolus) in Trial 2 could be given if necessary. During dexmedetomidine infusion, rescue medications were limited to propofol (0.2 mg/kg IV boluses) in Trial 1 and midazolam (0.2-mg/kg IV boluses) in Trial 2 for sedation and morphine for pain (2-mg IV boluses). After extubation, paracetamol was to be permitted for pain as clinically indicated. Propofol and midazolam were to be given only after increasing the dexmedetomidine infusion rate. Dexmedetomidine administration in Parts I and II was to begin within 1 hour of admission to the ICU and to be continued for 6 hours after extubation to a maximum of 24 hours total study drug infusion. Patients were observed and assessed for an additional 24 hours after cessation of dexmedetomidine.

The conclusions from the Trials 1 and 2 are as follows. The patients treated with dexmedetomidine required significantly less propofol (Trial 1) or midazolam (Trial 2) for sedation or morphine for pain than patients who received placebo. The sedation levels for dexmedetomidine-treated patients were achieved more quickly than those for placebo-treated patients who received propofol or midazolam. Dexmedetomidine was safe and well tolerated: the adverse events and laboratory changes reported in these studies were to be expected in a postsurgical population.

During Trial 1, Part I three dexmedetomidine-treated patients died, and during Trial 1, Part II, three dexmedetomidine-treated patients died and one placebo-treated patient died. However, none of the adverse events leading to death were considered to be related to dexmedetomidine administration. No deaths occurred among dexmedetomidine-treated patients in Part I and Part II of Trial 2, but five placebo-treated patients died. Dexmedetomidine produced changes in systolic blood pressure, diastolic blood pressure, and heart rate consistent with the known pharmacological effect of $\alpha_2$-agonists. Further, dexmedetomidine produced no clinically apparent respiratory depression after cessation of assisted ventilation.

The following 16 cases are from the above mentioned Part II of trials 1 and 2. The cases indicate that dexmedetomidine has analgesic properties and provides effective sedation and anxiolysis while allowing patients to remain oriented and communicative.

1. A 86-year-old female patient underwent abdominal resection due to a tumor in the colon. Surgery was performed with a short-acting analgesia (remifentanil). The patient was a non-smoker and had no cardiac history apart from elevated blood pressure. On arrival in the ICU, she required two doses each of morphine and midazolam. Dexmedetomidine was started at a loading dose of 6 μg/kg/h for 10 minutes and was maintained at a rate of 0.4 μg/kg/h for 30 minutes, followed by a mean dose of 0.5 μg/kg/h. The patient's Ramsay Sedation Score was 6 during the first hour, then decreased to 3 and, later, to 2. While receiving dexmedetomidine, the patient required only one dose of morphine 5 minutes before extubation. Extubation was performed at 6.5 hours and was uneventful.

2. A 66-year-old male patient underwent lobectomy of the right lung. The patient was formerly a heavy smoker (three packs a day) but had stopped 10 years previously. He had a history of daily alcohol intake, severe respiratory insufficiency and heart failure. On admission to the ICU, he was given a loading dose of dexmedetomidine of 6 µg/kg/h for 10 minutes, followed by an infusion at a rate of 0.2 to 0.7 µg/kg/h (titrated to the desired level of sedation) for 12 hours. Two hours after the start of the infusion, the patient exhibited hypotension (blood pressure of 70/40 mm Hg), but this resolved after crystalloid infusion without the need for vasopressor drugs. The patient recovered spontaneous ventilation 6 hours after surgery and was extubated at 6 hours and 15 minutes. The patient required no morphine or other analgesic during the 12-hour dexmedetomidine infusion. He did require morphine for pain after the infusion was terminated.

3. A 68-year-old male patient was admitted to the ICU after undergoing coronary artery bypass surgery for three-vessel disease. He had non-insulin-dependent diabetes mellitus and a history of atrial fibrillation and myocardial infarction. He was a nonsmoker who drank a glass of wine per day. Dexmedetomidine was administered at a loading dose of 6 µg/kg/h for 10 minutes followed by a maintenance dose of 0.2 to 0.3 µg/kg/h. The patient required no midazolam or morphine while receiving dexmedetomidine. His Ramsay Sedation Score was 6 during the first hour (baseline score, i.e., the patient was fully anaesthetized after surgery), then decreased to 4 and subsequently reached 3. A transient increase in blood pressure occured one hour into the postoperative course. The patient was extubated at approximately 6 hours, and his blood pressure increased again after the dexmedetomidine infusion was discontinued.

4. A 55-year-old male patient with a history of alcohol abuse underwent surgery for head and neck cancer. A dexmnedetomidine infusion (0.5 to 0.7 µg/kg/h) was started when the patient arrived in the ICU. He maintained hemodynamic stability throughout the infusion and exhibited no withdrawal symptoms. He required only 2 mg of morphine and 2 mg of midazolam immediately after extubation.

5. A 47-year-old male patient with a history of high alcohol intake underwent removal of a pharyngeal tumor and reconstruction with a jejunal flap. The surgical procedure lasted 10 hours during which the patient lost 3000 ml of blood and required transfusion of six units of blood. In the ICU, dexmedetomidine was administered in a loading dose of 6 µg/kg/h for 10 minutes followed by maintenance doses of 0.4 µg/kg/h for 35 minutes, 0.6 µg/kg/h for 20 minutes, and then 0.7 µg/kg/h for the remainder of the infusion. The patient remained calm and cooperative while receiving dexmedetomidine and his Ramsay Sedation Score was easily maintained between 2 and 3. He received a 2 mg dose of midazolam at 46 minutes and again at 66 minutes after the start of the dexmedetomidine infusion. Considering the nature of the surgery and the patient's history of alcohol consumption, initial postoperative morphine requirements were quite modest (24 mg). Yet, the morphine dose required escalated to 76 mg after the infusion of dexmedetomidine was discontinued.

6. A 35-year-old male patient with a history of "binge" drinking suffered bilateral lung contusions, several cracked ribs, and a large pelvic fracture in a traffic accident. He had uneventful general anesthesia during a 6-hour operation to repair his fractured pelvis. The blood loss was 400 ml, requiring a six-unit blood transfusion with cell saver. The patient received 70 mg of morphine intraoperatively. In the ICU, dexmedetomidine was administered at a loading dose of 6 µg/kg/h for 10 minutes.

The maintenance infusion was initiated at a rate of 0.4 µg/kg/h and was increased to 0.7 µg/kg/h during the first 3 hours. The patient's Ramsey Sedation Score was maintained at approximately 4. He was calm, comfortable, and required no morphine or midazolam. The patient was eligible for extubation at 6 hours. However, as this occured at 2:00 am, a decision was made to continue mechanical ventilation until the following morning. The dexmedetomidine dose varied between 0.3 and 0.5 µg/kg/h for approximately the final 160 minutes of the infusion.

The patient was awake, alert, and able to communicate in writing that he wanted the endotracheal tube removed. When the maximum allowable dose of dexinedetomidine, per protocol, was reached and when the patient became agitated and insistent over the removal of his endotracheal tube, doses of midazolam (totaling 16 mg) were administered. Despite his agitation, the patient remained free of pain and required no morphine while on dexmedetomidine. After extubation and cessation of the dexmedetomidine infusion, the patient required 4 mg of morphine before discharge from the ICU and nearly 50 mg of morphine during the first few hours after he returned to the ward. This need for more analgesia was considered a physiological response to pain, rather than a rebound effect.

7. A 60-year-old male alcoholic (35 units per week with fatty changes on liver ultrasound) underwent repair of an abdominal aortic aneurysm. He had a 40-year history of smoking, hypertension, angina pectoris, and pulmonary fibrosis. The surgery was technically difficult and took 3 hours. Blood loss was 3100 ml, and 6 units of blood were transfused. Morphine (30 mg) was administered intraoperatively. The patient was haemodynamically stable on arrival in the ICU. Dexmedetomidine was started at a loading dose of 6 µg/kg/h for 10 minutes followed by a maintenance dose of 0.4 µg/kg/h titrated to 0.7 µg/kg/h by the second hour. The Ramsey Sedation Score was maintained at approximately 4. Morphine requirements fluctuated markedly during the patient's first 6 hours in the ICU.

The patient was awake, oriented, and able to communicate that he was experiencing significant pain. At approximately 7 hours, with the dexmedetomidine dose at 0.5 µg/kg/h, it was determined that the entire graft was tearing off and the bottom disintegrating and pulling away from the posterior abdominal wall. Morphine requirements continued to escalate due to ongoing bleeding. The use of higher infusion rates of dexmedetomidine was limited by the presence of haemodynamic instability as a consequence of the bleeding. The patient was subsequently returned to surgery. Timely surgical intervention was facilitated by the patient's ability to communicate the breakthrough pain he experienced while receiving dexmedetomidine.

8. A patient underwent rectal extirpation and colostomy placement. Propofol was used for induction of anesthesia and oxygen/nitrous oxide/isoflurane for maintenance. In addition, remifentanil was started just after induction and continued until after the patient arrived in the ICU. A propofol infusion (70 mg) was also administered as the patient was transported to the ICU. By the time the patient arrived in the ICU, he was awake but agitated and restless with a Ramsey Sedation Score of 1. Propofol and remifentanil were stopped within minutes of the patient's arrival. Repeated bolus doses of propofol 10 mg were required to manage the patient's agitation. A dexmedetomidine loading dose (0.4 μg/kg/h) was administered with propofol 20 mg at approximately 25 minutes after arrival in the ICU and was followed by infusions of dexmedetomidine 0.7 μg/kg/h and propofol 4 mg/kg/h. Repeated doses of morphine 2 mg were required during the first 20 minutes of dexmedetomidine infusion. The patient's Ramsey Sedation Score continually increased until the patient was oversedated with a score of 6. Approximately two hours after arrival in the ICU, the propofol infusion was reduced to 2 mg/kg/h and subsequently to 1 mg/kg/h. At 3 hours, propofol was discontinued and the dexmedetomidine infusion was tapered to 0.2 μg/kg/h. No additional propofol or morphine was required.

This case illustrates the importance of administrating dexmedetomidine before the analgesics administered pre-ICU have has lost their effect. This is particularly important when an agent with a very short half-life, such as remifentanil, is used. Experience with intraoperative remifentanil, in particular, has shown that due to its very rapid offset, postoperative pain is perceived early, thereby increasing the requirement for postoperative analgesia.

9. A 60-year-old man with renal carcinoma underwent an uncomplicated 3-hour radical nephrectomy. He had no significant previous medical history. During surgery, he received balanced anesthesia. Postoperatively, the patient was comfortable, experienced no respiratory difficulties, and was discharged from the ICU the following day. While receiving dexmedetomidine, he had a Ramsey Sedation Score of 3. He had no major gas exchange problems and $PaCO_2$ was stable during mechanical ventilation, assisted spontaneous breathing, extubation, and spontaneous breathing. His breathing pattern was essentially unchanged in the immediate postoperative period, while on assisted spontaneous breathing and after extubation. This patient's experience exemplifies the absence of a respiratory depressant effect with dexmedetomidine.

10. A 58-year-old female patient was scheduled for double coronary bypass surgery. Her past history revealed high blood pressure, angina pectoris, and type II diabetes. Intraoperatively, she received sufentanil, midazolam, pancuronium, and propofol. She arrived in the ICU at 7:20 pm and received a bolus of 1 μg/kg of dexmedetomidine over 10 minutes followed by an infusion of 0.4–0.7 μg/kg/h. Extubation took place at 7:50 am the next morning and dexmedetomidine was continued until 1:40 pm. She had an uneventful post-operative course. While on dexmedetomidine and intubated, she had a Ramsey Sedation Score of 4. She was calm, easily arousable, and well- oriented. She was not frightened by her surroundings (noises, personnel, and monitoring devices). After extubation, the dexmedetomidine infusion was progressively decreased to 0.3 μg/kg/h and her Ramsey Sedation Score oscillated between 2 and 3. She remained calm, cooperative and had no respiratory depression. She required no additional sedatives and very little analgesia during the dexmedetomidine infusion. After the dexmedetomidine infusion was stopped, she became restless, uncomfortable, and loquacious. Her anxiety profile differed considerably on and off medication. When questioned, she had no amnesia of her ICU stay, yet exhibited no distress or unpleasant recall.

11. A 54-year-old male patient underwent quadruple coronary bypass surgery. He had a 35-year history of excessive alcohol intake, but had reduced his consumption during the 6 weeks preceding surgery. Even though alcoholic patients commonly exhibit increased levels of anxiety and agitation in the ICU, this individual had an excellent postoperative course while receiving dexmedetomidine. He remained calm and quiet, yet well oriented. The dexmedetomidine infusion was maintained between 0.3 and 0.7 μ/kg/h and no additional sedatives were required. He was extubated the evening of his surgery, however, the dexmedetomidine infusion was continued until the next morning. On questioning, he indicated that he was extremely satisfied with his stay in the ICU.

12. A 49-year-old female patient underwent aortic valve replacement through a Ross procedure. The patient was unaware of her cardiac condition until the week preceding her surgery, was not psychologically prepared, and exhibited a high degree of anxiety preoperatively. On arrival in the ICU, she received a dexmedetomidine bolus of 1 μg/kg over a 10-minute period followed by a dexmedetomidine infusion between 0.2–0.5 μg/kg/h. She was extubated the evening of her surgery and dexmedetomidine was continued through until the next morning. During her postoperative course, the patient was calm, had no fear or apprehension, and was well oriented even though she had a little amnesia. She had excellent evolution and was very comfortable with her ICU experience.

13. The patient was a hypertensive, 51-year-old male with nephrolithiasis and a "silent" left kidney. He was admitted for a nephrectomy. Comorbidities included a hiatal hernia, gastric ulcer and diverticulum, and hepatic fatty metamorphosis. Other than these abnormalities, physical examination was within normal limits. His operative course and anaesthetic course were uneventful and he reached the ICU with a baseline Ramsey Sedation Score of 4. The desired level of sedation was very easily achieved with little dose adjustment of the infused dexmedetomidine as shown in FIG. 2. The patient could be easily roused and was able to communicate his needs to the nursing staff. Despite the presence of an endotracheal tube, he remained calm and asleep when free of external stimuli. The patient was extubated at 6 hours after ICU admission. Despite frequent assessments of his pain and opportunities to request additional analgesia, he required only a single dose (2 mg) of morphine sulfate at 6 hours into the study period. His postoperative course was uneventful except for one episode of moderate hypotension 14 hours after the initiation of dexmedetomidine administration and nearly 3 hours after the discontinuation of dexmedetomidine infusion. The patient responded to crystalloid infusion and the episode was attributed by the physician to the effects of morphine and possibly a mild volume deficit. Post-study, the patient's only complaint was somatic pain at the incision site. When interviewed, the patient stated that although the presence of the endotracheal tube was uncomfortable, were he to be readmitted to the unit he would request the same sedative he had received during the present hospitalization.

14. A 42-year-old male who had undergone coronary artery bypass surgery arrived in the ICU with a Ramsey Sedation Score of 5 (asleep, sluggish responses to light glabellar tap or loud auditory stimuli). A loading dose of dexmedetomidine 6 µg/kg/h was administered followed by maintenance infusion at a dose of 0.4 µg/kg/h. The patient had a Ramsey Sedation Score of 6 (asleep, no response) for the first half hour. However, the infusion was rapidly and easily titrated to achieve and maintain a score of 2 (cooperative, oriented, tranquil) or a score of 3 (patient responds to commands) during the remainder of his stay in the ICU. No evidence of haemodynamic instability was observed and no opiate was required. The patient was extubated at approximately 6 hours and the rest of his ICU course was uneventful. He experienced moderate pain after extubation and the pain was easily controlled with a single injection of morphine 2 mg.

15. A 58-year-old male underwent valve replacement for aortic stenosis. In the ICU, he received a dexmedetomidine infusion titrated to achieve a Ramsey Sedation Score of approximately 3. He was oriented and cooperative. At one point, the infusion rate was increased because the patient began to experience pain. Importantly, he was able to communicate his need for pain relief, and dose titration rapidly restored his comfort rapidly.

16. The patient was a 62-year-old male, New York Heart Association class III with aortic regurgitation, left ventricular hypertrophy, and a dilated ascending aorta. He also had arterial hypertension and exertional angina (Canadian class II) with a normal coronary arteriogram. His preoperative medication was propranolol. The patient underwent normothermic cardiopulmonary bypass with replacement of the aortic valve and a Bentall procedure. He was weaned uneventfully from the pump after the 6-hour procedure and received no postoperative inotropic support. The course in the ICU was uneventful. The hemodynamic profile was smooth without hypotension or episodes of bradycardia. Although the patient did show an increase in blood pressure following discontinuation of dexmedetomidine, he entered the study with established hypertension.

The cases described above illustrate the benefits of dexmedetomidine sedation in critically ill patients. Appropriately sedated, the patients were oriented, physiologically stable and experiencing minimal pain, discomfort and anxiety. It is current practice to stop sedative drugs during ventilator weaning and after extubation to avoid respiratory depression. Such practice is not necessary with dexmedetomidine. Furthermore, dexmedetomidine increases patient compliance with therapeutic interventions (e.g., mobilization or chest physiotherapy) by removing fear of pain. This is a remarkable constellation of effects for a single medication.

Those skilled in the art will recognize that while specific embodiments have been illustrated and described, various modifications and changes may be made without departing from the spirit and scope of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of sedating a patient in an intensive care unit, which comprises administering to the patient an effective amount of dexmedetomidine of a pharmaceutically acceptable salt thereof, wherein the patient remains arousable and orientated.

2. The method according to claim 1, wherein the dexmedetomidine or pharmaceutically acceptable salt is the sole active agent.

3. A method of sedating a patient in an intensive care unit, comprising administering a pharmaceutical composition to the patient, wherein the pharmaceutical composition comprises an active agent and an inactive agent, wherein the active agent consists of dexmedetomidine or a pharmaceutically acceptable salt thereof, ane wherein the patient remains arousable and orientated.

4. The method according to claim 1, wherein the dexmedetomidine pharmaceutically acceptable salt thereof is administered in an amount to achieve a plasma concentration of 0.1–2 ng/ml.

5. The method according to claim 4, wherein the dexmedetomidine or pharmaceutically acceptable salt thereof is administered intravenously.

6. The method according to claim 5, wherein a loading dose and a maintenance dose of dexmedetomidine are administered.

7. The method according to claim 6, wherein the patient is a human.

8. The method according to claim 7, wherein the loading dose of dexmedetomidine is 0.2–2 µg/kg.

9. The method according to claim 8, wherein the loading dose is administered in about 10 minutes.

10. The method according to claim 7, wherein the maintenance dose of dexmedetomidine is 0.1–2.0 µg/kg/h.

11. The method according to claim 10, wherein the maintenance dose is 0.2–0.7 µg/kg/h.

12. The method according to claim 11, wherein the maintenance dose is 0.4–0.7 µg/kg/h.

* * * * *

UNITED STATES PATENT AND TRADEMARK OFFICE
CERTIFICATE OF CORRECTION

PATENT NO. : 6,716,867 B1 Page 1 of 1
DATED : April 6, 2004
INVENTOR(S) : Riku Aantaa et al.

It is certified that error appears in the above-identified patent and that said Letters Patent is hereby corrected as shown below:

Title page,
Item [57], ABSTRACT,
Line 3, "of a" should read -- or a --.
Item [73], Assignee, add second assignee -- Abbott Laboratories, Abbott Park, IL (US) --

Column 14,
Line 15, "dexmedetomidine of" should read -- dexmedetomidine or --.
Line 26, "ane" should read -- and --.
Line 29, "pharmaceutically" should read -- or pharmaceutically --.

Signed and Sealed this

Twenty-fifth Day of May, 2004

JON W. DUDAS
*Acting Director of the United States Patent and Trademark Office*